United States Patent [19]

Hefner et al.

[11] Patent Number: 5,554,777
[45] Date of Patent: Sep. 10, 1996

[54] CATALYST FOR THE PREPARATION OF LINEAR CARBON MONOXIDE/ALPHA-OLEFIN COPOLYMERS

[75] Inventors: John G. Hefner; Brian W. S. Kolthammer, both of Lake Jackson, Tex.

[73] Assignee: The Dow Chemical Compamy, Midland, Mich.

[21] Appl. No.: 272,727

[22] Filed: Jul. 8, 1994

Related U.S. Application Data

[63] Continuation-in-part of Ser. No. 9,198, Jan. 22, 1993, abandoned.

[51] Int. Cl.$^6$ .............................. C07F 9/02; C07F 15/00; B01J 31/00
[52] U.S. Cl. .................. 556/21; 556/30; 556/136; 556/137; 502/162; 502/167
[58] Field of Search ............................. 556/21, 30, 136, 556/137; 502/162, 167

[56] References Cited

U.S. PATENT DOCUMENTS

| | | | |
|---|---|---|---|
| 2,577,208 | 12/1951 | Reepe et al. | 260/406 |
| 3,654,279 | 4/1972 | Hurley et al. | 250/370 |
| 3,689,460 | 9/1972 | Nozaki | 260/63 CQ |
| 3,781,321 | 12/1973 | Hurley, Jr. et al. | 260/453 |
| 3,835,123 | 9/1974 | Nozaki | 260/94.9 B |
| 3,984,388 | 10/1976 | Shryne et al. | 260/63 CQ |
| 4,804,738 | 2/1989 | Drent | 528/392 |
| 4,804,739 | 2/1989 | Drent | 528/392 |
| 4,818,810 | 4/1989 | Drent | 528/329 |
| 4,831,114 | 5/1989 | Drent | 528/329 |
| 4,835,250 | 5/1989 | Drent | 528/329 |
| 4,866,128 | 9/1989 | Gergen et al. | 525/92 |
| 4,874,736 | 10/1989 | Drent | 502/165 |
| 4,880,903 | 11/1989 | Van Broekhoven et al. | 528/392 |
| 4,885,376 | 12/1989 | Verkade | 556/18 |
| 4,889,913 | 12/1989 | Drent | 528/392 |
| 4,904,728 | 2/1990 | George | 525/64 |
| 4,921,938 | 5/1990 | Drent | 528/392 |
| 4,925,918 | 5/1990 | Brown et al. | 528/392 |
| 4,940,775 | 7/1990 | Drent | 528/392 |
| 4,954,570 | 9/1990 | Smutny | 525/185 |
| 4,970,294 | 11/1990 | Drent et al. | 528/392 |
| 5,010,171 | 4/1991 | Van Broekhoven et al. | 528/392 |
| 5,030,606 | 7/1991 | Klabunde | 502/155 |
| 5,030,712 | 7/1991 | Van Doorn et al. | 528/392 |
| 5,034,507 | 7/1991 | Smith | 528/392 |
| 5,055,552 | 10/1991 | Wong | 528/392 |
| 5,091,506 | 2/1992 | Drent et al. | 528/392 |
| 5,091,507 | 2/1992 | Van Leeuwen et al. | 528/392 |
| 5,102,844 | 4/1992 | Wong | 502/162 |
| 5,106,952 | 4/1992 | Drent | 528/392 |
| 5,115,094 | 5/1992 | Mastenbroek et al. | 528/392 |
| 5,162,493 | 11/1992 | Drent | 528/392 |
| 5,218,084 | 6/1993 | Klusener et al. | 528/392 |
| 5,292,700 | 3/1994 | Kluesner et al. | 502/167 |
| 5,310,871 | 5/1994 | Sommazzi et al. | 528/392 |
| 5,314,856 | 5/1994 | Sommazzi et al. | 502/167 |
| 5,324,701 | 6/1994 | Sommazzi et al. | 502/167 |
| 5,330,952 | 7/1994 | Drent . | |

FOREIGN PATENT DOCUMENTS

| | | |
|---|---|---|
| 0061337 | 9/1982 | European Pat. Off. . |
| 443687 | 8/1991 | European Pat. Off. . |
| 0450707 | 10/1991 | European Pat. Off. . |
| 0522643 | 1/1993 | European Pat. Off. . |
| 1081304 | 8/1967 | United Kingdom . |

OTHER PUBLICATIONS

Malik, *Chemical Abstracts*, vol. 78, No. 14, Abs. No. 91947 p, 1973.
Roeper et al., *Chemical Abstracts*, vol. 103, No. 16, Abs. No. 123983a, 1985.
A. Sen, *Organometallics*, 1982, pp. 415–417.
*Advances in Polymer Science*, 73/74 Springer–Verlag, New York, pp. 126–144, 1986.
*PCT International Search Report*, PCT/US 94/00245, 16 Jun. 1994.
Robert F. Schramm and Bradford B. Wayland, Chemical Communications, *Oxidation of Metallic Palladium by Nitrosyl Tetrafluoroborate*, pp. 898–899, 1968.
Bradford B. Wayland and Robert F. Schramm, Cationic and Neutral Chloride Complexes of Pd(II), *Cationic and Neutral Chloride Complexes of Palladium (II) with the Nonaqueous Solvent Donors Acetonitrile, Dimethyl Sulfoxide, and a Series of Amides, Mixed Sulfur and Oxygen Coordination Sites in a Dimethyl Sulfoxide Complex*, pp. 971–976, vol. 8, No. 4, Apr. 1969.
Peter M. Mathis, *The Organic Chemistry of Palladium*, vol. 1, p. 49, Academic Press, 1971.

*Primary Examiner*—Porfirio Nazario-Gonzales

[57] ABSTRACT

Novel catalyst compositions comprising a cationic transition metal complex containing palladium, a mono-, di-, or tridendate ligand, and an anion are disclosed. The novel catalyst compositions can be used in a process for polymerizing carbon monoxide and at least one ethylenically unsaturated hydrocarbon to produce linear alternating polymers. Processes for preparing the novel catalyst compositions are also disclosed.

9 Claims, No Drawings

CATALYST FOR THE PREPARATION OF LINEAR CARBON MONOXIDE/ALPHA-OLEFIN COPOLYMERS

CROSS REFERENCE TO RELATED APPLICATION

This is a continuation-in-part of application Ser. No. 08/009,198 filed Jan. 22, 1993, now abandoned, the teachings of which are expressly incorporated herein.

TECHNICAL BACKGROUND

This invention relates to the production of linear alternating polymers of carbon monoxide and at least one ethylenically unsaturated hydrocarbon. More particularly, the invention relates to a method of making novel catalyst compositions and a novel process for the production of such polymers employing the catalyst compositions in the process.

The invention relates to homogeneous catalysts for copolymerization of carbon monoxide and alpha olefins, methods for preparing these catalysts, and a process of copolymerizing alpha-olefins and carbon monoxide using these catalysts. More particularly, the invention relates to a homogeneous catalyst useful for making polymers containing carbon monoxide and olefins in interpolymerized form.

The process of producing linear alternating copolymers of carbon monoxide and ethylenically unsaturated compounds is described in U.S. Pat. No. 3,835,123 and U.S. Pat. No. 3,984,388. These polymers are represented by the general structural formula —A—B—A—B— (where A=olefin and B=carbonyl). When the olefin is ethylene the resulting polymer may be represented by the formula

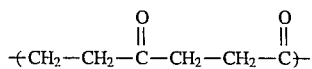

In the case where propylene is present in the reaction mixture, the polymer will have $C_3$ units randomly scattered through the olefinic portion of the polymer. The $C_3$ units do not interfere with or disrupt the linear alternating structure of the polymer in that only one olefinic unit is located between two carbonyl goups.

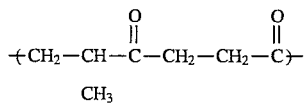

An improvement in the process of making carbon monoxide/α-olefin polymers was described in EPO applications 0 121 965 A2 and 0 181 014 A1. It was reported that more active catalysts resulted when the catalyst composition was based on Group VIII metals of the Mendeleev Periodic Table, an anion of a non-hydrohalogenated acid with a pKa of less than 2 and a bidentate ligand containing phosphorous, arsenic or antimony dentate groups which can complex with the metal. For example, Pd, Co or Ni are given as the transition metal sources with anions that could be used including hexafluorophosphate ($PF_6^-$), trichloroacetate and tetrafluoroborate ($BF_4^-$) which are respectively the conjugate anions of hexafluorophosphoric acid, trichloroacetic acid and tetrafluoroboric acid.

U.S. Pat. No. 4,804,739 describes the use of catalysts based on palladium as the transition metal source and quaternary phosphonium salts for the anion source. These catalysts reduce the amount of metallic residues in the product. The catalyst compositions generally consist of a palladium(II) salt (such as a halide or acetate), a strong organic acid (such as trifluoroacetic, p-toluenesulfonic acid) and a bidentate phosphine (such as, 1,3-bis[diphenylphosphino]propane).

U.S. Pat. No. 4,831,114 discloses the use of a catalyst containing a Group VIII metal, an anion of a non-hydrohalogenic acid having a pKa more than about 2 but less than 4, and certain bidentate hydrocarbyl phosphine ligands. The composition is described as exhibiting greater reactivity at lower reactor temperatures.

EPO application 0 396 268 A1 describes the use of a catalyst including a palladium(II) salt, a bidentate amine, phosphine, arsine or stibene and specified anions. Quinone was added as an oxidant to prevent reduction of the transition metal. Quinones are described as being useful in maintaining catalyst stability.

A different catalyst system for the polymerization of carbon monoxide and alpha olefins involves the use of cationic palladium (II) catalysts. Researchers have reported the use of a cationic palladium (II) compound $[Pd(CH_3CN)_4]^{+2} [(BF_4)]_2^-$ to polymerize styrene, α-methyl styrene, cyclohexene, norbornylene and norbornadiene under mild conditions. (Sen, *Organometallics* 1982, 1, 415–417). Cationic palladium (II) has been reported for ethylene/carbon monoxide polymerization using [bis(acetonitrile)palladium(II) 1,3 -bis(diphenylphosphino)propane] [bis(tetrafluoroborate)] and $[Pd(triphenylphosphine)_n(CH_3CN)_{4-n}](BF_4)_2$ (where n=1–3). *Advances in Polymer Science*, 73/74, Springer-Verlag, New York, 1986 pages 126–44.

Processing and fabrication of articles from ethylene/ carbon monoxide linear alternating copolymers produced by prior art processes and catalyst are difficult. The melting point of such copolymers is close to their thermal decomposition point, and this made thermal fabrication techniques difficult to control. This problem can be overcome by adding small amounts of propylene into the polymerization reaction mixture. The propylene is interpolymerized into the polymer backbone and decreases the melt point or temperature at which a reasonable melt flow will occur of the terpolymer product. U.S. Pat. Nos. 4,866,128 and 4,904,716 show that terpolymers prepared with a melting range of 220° to 235° C. are more useful for fabrication processes.

U.S. Pat. No. 4,866,128 teaches another approach for controlling the melting range of olefin/carbon monoxide polymers by blending them with other polymers. Only limited success has been achieved by this technique due to the apparent incompatibility of the ethylene/carbon monoxide copolymer with other materials, even under melt processing conditions. See, for example, U.S. Pat. Nos. 4,904, 728 and 4,954,570.

A need exists for a more versatile catalyst which can incorporate a larger variety of olefinic comonomers into the polymer at high catalyst efficiency and higher reaction rates. Such a catalyst would provide flexibility in controlling the melt flow characteristics of this polymer and terpolymers by varying the olefinic component and would permit the preparation of polymers which range from completely amorphous to highly crystalline.

There is also a need for a catalyst composition which does not require the presence of a strong acid component. Such a catalyst would have significant advantages, e.g., lower corrosion rate of process equipment and lower toxicity.

SUMMARY OF THE INVENTION

Novel catalyst compositions have now been discovered comprising a cationic transition metal complex of the formula $$(Pd(II)S_{4-ax}L_x)^{+2}(A)^{-n}_y$$

wherein:

Pd(II) is palladium having a valence of +2;

S is a synthesis solvent;

L is a monodendate, bidendate or tridendate ligand or ligands having one or more bonding sites;

x is an integer from 1 to 3 and is equal to the total number of ligand bonding sites;

A is a weakly or non-coordinating anion capable or stabilizing the complex in its cationic form; and a represent the number of bonding sites of the ligand L n is 1 or 2 and y is 2 or 1;

provided that (i) when n is 1, y is 2 and when n is 2, y is 1; and (ii) when the anion A is tetrafluoroborate, the organometallic complex is not (tris(acetonitrile)palladium(II)triphenylphosphine), (bis(acetonitrile)palladium(II)bis(triphenylphosphine)), ((acetonitrile)palladium(II)tris(triphenylphosphine)) or (bis(acetonitrile)palladium(II) 1,3-bis(diphenylphosphino)propane).

These catalyst compositions can be advantageously prepared by several methods. A first method of preparing the catalyst compositions comprises the steps of:

(a) contacting nitrosonium tetrafluoroborate and elemental palladium and a synthesis solvent to form a solution; and (b) admixing the solution with a mono-, bi-, tri-, or tetradentate ligand, under reaction conditions sufficient to form a cationic organometallic complex of palladium(II) and a weakly or non-coordinating anion.

A second method of preparing the catalyst composition comprises the steps of:

(a) contacting a strong acid and elemental palladium and a synthesis solvent to form a solution; and (b) admixing the solution with a mono-, bi-, tri-, or tetradentate ligand, under reaction conditions sufficient to form a cationic organometallic complex of palladium(II), and a weakly or non-coordinating anion.

A third method of preparing the catalyst compositions comprises the steps of:

(a) contacting a palladium dihalide and a metal containing salt and a synthesis solvent to form a solution; and (b) admixing the solution with a mono-, bi-, tri-, or tetradentate ligand, under reaction conditions sufficient to form a cationic organometallic complex of palladium(II), and a weakly or non-coordinating anion.

The new catalyst compositions are useful for the copolymerization of carbon monoxide and at least one ethylenically unsaturated hydrocarbon to produce linear alternating polymers. The rate of polymerization is enhanced by including an alcohol, such as methanol, in the polymerization mixture.

DETAILED DESCRIPTION OF THE INVENTION

The catalyst compositions of the current invention are generally prepared by reacting together a source of palladium, appropriate solvent and anion followed by partial or complete substitution of the solvent by an appropriate ligand. The anion is preferably that of a strong acid, i.e., an anion of an acid having a pKa of less than 2 for those acids having a measurable pKa, and preferably consists of tetrafluoroborate, tetraphenylborate, perchlorate, hexafluorophosphate, trifluoromethanesulfonate, or a mixture thereof. Depending on the method of catalyst preparation, either metallic palladium or a palladium dihalide (except palladium difluoride) is preferred as the source of the palladium.

The solvent used in the synthesis of the catalyst must not decompose the palladium metal complex or any of the reactants. Depending on the method of catalyst preparation, described below, the following compounds are useful as synthesis solvents: acetonitrile, benzonitrile, propionitrile, 1,4-dioxane, dimethylformamide, hexamethylphosphoramide, pyridine, 1-piperidinecarbonitrile, dimethoxyether, aniline, dimethylsulfoxide, 1,2-dimethoxyethane, diethylether, tetrahydrofuran, or a mixture of at least two thereof.

The source of anion is preferably that of a strong acid. Examples of acids and salts are nitrosium tetrafluoroborate, tetrafluoroboric acid, silver perchlorate, perchloric acid, sodium tetraphenylborate, sodium hexafluorophosphate, silver trifluoromethanesulfonate, and the like.

The ligands used to partially or completely displace the synthesis solvent molecules can be mono-, bi, tri- or tetradentate. Suitable coordinating ligands include, for example, aliphatic or aromatic substituted nitrogen containing compounds, phosphines, arsines and stibines. Preferably the ligand or ligands employed are substantially water insoluble, meaning in this context and in the claims that the resulting catalyst complex is less soluble in water than in a non-aqueous inert solvent useful for dissolving the catalyst in the process described herein for producing alternating linear copolymers of carbon monoxide and at least one alpha olefin. More preferably, the coordinating ligand is 1,3-bis(diphenylphosphino)propane or 1,1,1-tris(diphenylphosphinomethyl)ethane.

Ligands can be employed in the catalyst compositions which are generally covalently bound nucleophilic groups to the palladium atom and provide stability to the complex. These are selected from monodentate, bidentate or tridentate ligands of nitrogen, phosphorus, arsenic or antimony. Suitable monodentate ligands are of the formula $$R^1R^2R^3Z$$

wherein $R^1$, $R^2$ and $R^3$ are independently organic radicals of from 1 to 20 carbon atoms selected from a group consisting of akyl, aryl, alkaryl or alkoxyaryl. Preferably each aryl, alkaryl or alkoxyaryl of consists of 6 to 14 carbon atoms. Examples of such organic radicals are phenyl, p-methylphenyl, o-methoxyphenyl, p-methoxyphenyl, o-dimethoxyphenyl and 2,6-dimethylphenyl. Suitable atoms for Z include nitrogen, phosphorus, arsenic and antimony, preferably nitrogen or phosphorus. Examples of monodentate ligands include triphenyl phosphine, diphenylmethylphosphine, dimethylphenylphosphine, tris(o-methoxyphenyl)phosphine, tris(2,6-dimethoxyphenyl)phosphine, tris(p-methoxyphenyl)phosphine, tris(p-methylphenyl)phosphine and tris(2,6-dimethylphenyl)phosphine, mixtures thereof and the like.

Suitable bidentate ligands are of the formula $$R^1R^2—Z—R^4—Z—R^1R^2$$

wherein $R^1$ and $R^2$ are the radicals previously defined. Examples of such organic radicals are phenyl, p-methylphenyl, o-methoxyphenyl, p-methoxyphenyl, o-dimethoxyphenyl and 2,6-dimethylphenyl. The $R^4$ group is a divalent aryl or alkaryl organic group of from 2 to 20 carbon atoms with preferably two or three carbon atoms separating Z. Suitable atoms for Z include nitrogen, phosphorus, arsenic and antimony, preferably nitrogen or phosphorus. Examples of bidentate ligands include:

1,2-bis(diphenylphosphino)ethane,
1,3-bis(diphenylphosphino)propane,
1,3-bis[bis(o-methoxyphenyl)phosphino]propane,
1,3-bis[bis(2,6-dimethoxyphenyl)phosphino]propane,
1,3-bis[bis(p-methoxyphenyl)phosphino]propane,
1,3-bis[bis(p-methylphenyl)phosphino]propane and
1,3-bis[bis(2,6-dimethylphenyl)phosphino]propane, mixtures thereof, and the like.

Suitable tridentate ligands are preferably of the formula

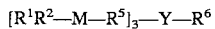

$[R^1R^2-M-R^5]_3-Y-R^6$ wherein $R^1$ and $R^2$ are the radicals previously defined. Examples of such organic radicals are phenyl, p-methylphenyl, o-methoxyphenyl, p-methoxyphenyl, o-dimethoxyphenyl and 2,6-dimethylphenyl. The $R^5$ group is a divalent radical with preferably one or two carbon atoms, M is any trivalent group such as nitrogen, phosphorus, arsenic, or antimony. Y is nitrogen, phosphorus, arsenic and $R^6$ is not present or if Y is carbon, then $R^6$ is any organic radical of from 1 to 20 carbon atoms or hydrogen. Examples of tridentate ligands include:

1,1,1-tris(dimethylphosphinomethyl)ethane,
tris(dimethylphosphinomethyl)methane,
1,1,1-tris(dimethylphosphinomethyl)propane,
tris(diphenylphosphinomethyl)methane,
1,1,1-tris(diphenylphosphinomethyl)ethane,
1,1,1-tris(diphenylphosphinomethyl)propane,
tris(diphenylphosphinoethyl)methane,
N,N,N-[tris(diphenylphosphinomethyl)]amine,
N,N,N-[tris(diphenylphosphinoethyl)]amine,
1,1,1-tris[bis(2,6-dimethoxyphenyl)phosphinomethyl] ethane,
1,1,1-tris[bis(2,6-dimethylphenyl)phosphinomethyl] ethane,
N,N,N-[tris[bis(2,6-dimethoxyphenyl)phosphinomethyl]] amine,
N,N,N-[tris[bis(2,6-dimethylphenyl)phosphinomethyl] amine, combinations thereof, and the like.

The palladium tetrafluoroborate compositions can be prepared by contacting metallic palladium with a slight excess of nitrosonium tetrafluoroborate in a suitable synthesis solvent which is compatible with the oxidizing agent followed by partial or complete displacement of this solvent with a coordinating ligand. Suitable synthesis solvents include, for example, acetonitrile, benzonitrile, propionitrile, dimethoxyethane, 1,4-dioxane, and combination thereof, and the like. The reaction is preferably conducted using a slight stoichiometric excess of nitrosonium tetrafluoroborate by contacting the reactants at any temperature which doesn't decompose the reactants or products. Preferably the reaction is conducted at room temperature under an inert atmosphere.

Another method for generating the palladium metal complex involves the direct reaction of palladium metal with an oxidizing acid, for example, trifluoromethanesulfonic acid, tetrafluoroboric acid or more preferably perchloric acid in the appropriate synthesis solvent followed by partial or complete displacement of the solvent with a coordinating ligand. The oxidizing acid must be capable of oxidizing the palladium metal from Pd(0) to Pd(II). The synthesis solvents include, for example, but are not limited to dimethylsulfoxide, hexamethylphosphoramide, dimethylformamide, acetonitrile, propionitrile, benzonitrile, 1-piperidinecarbonitirle, pyridine, aniline, dimethoxyethane, diethyl ether, tetrahydrofuran, 1,4-dioxane, or any other combination thereof and the like. The reaction is preferably conducted with palladium in the presence of a slight excess of the acid component.

The palladium metal complex may also be generated by the reaction of a palladium dihalide with a metal containing salt in the appropriate solvent using salt elimination as the driving force followed by partial displacement of the solvent with a coordinating ligand. For example, the palladium dihalide may be comprised of either Cl, Br or I. The metal salt may consist for example of lithium, sodium, potassium or silver and the anion of an acid such as tetraphenylborate, perchlorate, nitrate or hexafluorophosphate. Suitable examples of metal containing salts include sodium tetraphenylborate, silver tetraphenylborate, silver perchlorate, sodium nitrate, silver nitrate, sodium hexafluorophosphate, silver trifluoromethanesulfonate and potassium hexafluorophosphate. The synthesis solvents include for example, but are not limited to dimethylformamide, hexamethylphosphoramide, pyridine, acetonitrile, benzonitrile, propionitrile, 1-piperidinecarbonitrile, 1,2-dimethoxyethane, tetrahydrofuran, aniline, dimethylsulfoxide, 1,4-dioxane, or any other combination thereof and the like.

For the preparation of carbon monoxide/olefin polymers according to this invention, the polymerization reaction is preferably carried out by contacting the monomers and catalyst in a liquid phase or in a gas phase using methods commonly employed by industry. The quantity of catalyst used can vary within wide limits. Preferably the quantity of catalyst used will contain from $1\times10^{-1}$ mol of palladium to about $1\times10^{-6}$ mol of palladium per liter of polymerization solvent.

In the process of the current invention, carbon monoxide is polymerized with at least one ethylenically unsaturated hydrocarbon (i.e., alpha olefins) using the novel catalyst composition described herein. Hydrocarbons having from 2 to 20 carbon atoms are preferred, with those having from 2 to 10 being more preferable. These hydrocarbons include α-olefins such as ethylene, propylene, butene, 4-methyl-1-pentene, hexene, octene, decene, styrene or p-methylstyrene. The preferred alpha-olefins are ethylene and/or propylene.

An activator can be employed along with the catalyst composition in the polymerization process. Activators are generally alkanols such as methanol. Although not wishing to be bound by theory, evidence from mass spectra of decomposed polymer fragments suggests that the alcohol serves as a telogen in the reaction mixture. Enhanced reaction rates are observed when an alcohol is present which further suggests it may serve to initiate and/or terminate polymerization. The alcohol can also serve as the polymerization solvent, however, decreased reaction rates are observed for catalysts containing weakly coordinating anions such as $BF_4^-$. The preferred molar ratio of alcohol: palladium ranges from about 1:1 to about 1,000,000:1 with the most preferred range being from about 100:1 to about 100,000:1. Suitable alcohols include, for example, lower alkanols of 1–4 carbon atoms, such as methanol, ethanol, n-propanol, isopropanol, n-butanol, s-butanol and t-butanol.

Suitable reaction pressures for the polymerization range from about 1 atmosphere to about 700 atmospheres with the preferred range being from about 7 atmospheres to about 300 atmospheres. In the polymerization reaction it is preferred that the partial pressure ratio of the olefins:carbon monoxide (where the olefin component is ethylene and/or propylene) ranges from about 1:2 to 1:20 and preferably from about 1:4 to 1:10.

The polymerization reaction is normally conducted in an "inert solvent." As used in this context, by "inert solvent" is meant one which dissolves the catalyst composition without decomposition or displacement of the ligands at elevated temperature and pressure. The inert solvent may, however, comprise a component, e.g., a lower alkanol, which may affect the rate of initiation, chain termination, or chain transfer reactions in the polymerization process. A solvent with low vapor pressure at reaction temperatures is desirable to eliminate the need for higher reactor pressures. Suitable solvents include ethers, diethers, cyclic ethers, ketones, diketones, alkanols, aromatic hydrocarbons, halogenated hydrocarbons, aromatic amines and nitriles. Examples of such solvents include diethyl ether, dimethoxyethane, 1,4-dioxane, tetrahydrofuran, acetone, methylethylketone, dimethylsulfoxide, methanol, ethanol, n-propanol, isopropanol, n-butanol, s-butanol, t-butanol, toluene, xylene, carbon tetrachloride, chloroform, methylene chloride, 1,2-dichloroethane, acetonitrile, propionitrile, piperidinecarbonitrile, benzonitrile, aniline, pyridine, any combinations thereof, and the like.

Solvent selection and reaction temperature have an effect on polymer tacticity when the olefin group contains more than two carbon atoms, particularly when the anion is non-coordinating, such as $BF_4^-$. For example, acetone as a solvent at a temperature of 30° C. or less gives a more tactic polymer than 1,2-dichloroethane under similar reaction conditions. Increasing the reaction temperature to at least 65° C. gives essentially an atactic copolymer independant of the solvent.

The polymerization rate is affected by the counterion present in the catalyst. When the anion is non-coordinating, such as $BF_4^-$, the polymerization reaction rate is lower in polar solvents than in non-polar solvents. Analogously, when the anion is strongly coordinating, such as perchlorate, the reaction rate is generally higher in polar solvents than in less polar solvents.

Reactors may include those employed in the industry for the particular method of polymerization being used. Suitable reaction temperatures preferably include those which give significant reaction rates without decomposition of the catalyst. Furthermore, temperature can affect the molecular weight and tacticity of the polymers depending on the reaction mixture employed. The reactants, carbon monoxide and alpha-olefins, are highly reducing to Pd(II) and the reduction rate increases with increasing temperature. In general, all catalysts are more easily reduced at elevated temperatures. Polymerization can occur over a range of −78° C. to 200° C. with the most preferred range being 25° C. to 150° C. Increasing reaction temperature also increases the rate of polymerization provided that catalyst deactivation is not significant. For example, catalysts having $BF_4^-$ as the anion are less stable at reactor temperatures above 100° C. than those having perchlorate which shows virtually no loss in reaction rate after more than 7 hours at 80° C. Deactivation of the catalyst may occur by decomposition or any other mechanism which destroys the ability of the catalyst to promote the desired reaction.

EXPERIMENTAL

All catalyst complexes were prepared under dry nitrogen which was passed through a column of reduced chromium on PA-400 Davidson refrigeration grade silica to remove the last traces of water and oxygen. Acetonitrile, propionitrile, benzonitrile, dimethylforamide and hexamethylphosphoramide were purchased as anhydrous when available or high purity from Aldrich Chemical Company and used without further purification. Palladium powder, nitrosonium tetrafluoroborate, silver perchlorate, palladium dichloride, sodium hexaphophate, silver trifluoromethanesulfonate and sodium tetraphenylborate were purchased from Aldrich Chemical Company and were used without further purification. N,N,N',N'-tetramethyl-1,3-propanediamine was purchased from Aldrich Chemical Company and refluxed over calcium hydride under dry nitrogen followed by distillation from calcium hydride. Tris(o-methoxyphenyl)phosphine and 1,3-bis(diphenylphosphino)propane were purchased from Strem Chemical Company and used without further purification with the exception of some impure batches of 1,3-bis(diphenylphosphino)propane purchased from Aldrich which required crystallization from hot methanol. The 1,1,1-tris(dimethylphosphinomethyl)-ethane and 1,1,1-tris-(diphenylphosphinomethyl)ethane ligands were prepared by adapted literature methods (Maier, L. *J. Inorg. Nucl. Chem.* 24, (1962) 275 and Whitesides, G. M. *J. Am. Chem. Soc.* 93, 6, (1971) 1379–1389). All complexes were stored and weighed in a Vacuum Atmospheres dry box equipped with an oxygen and water removal train.

Preparation of [tetrakis(acetonitrile)palladium(II)] [tetrafluoroborate], (I.)

A 250 mL vessel was charged in a dry box with palladium powder, 0.5 g (4.70 mmole), then transferred to a vacuum line. Acetonitrile was added, 50 mL, to form a slurry of finely divided metal which was stirred magnetically. A 100 mL vessel was charged in a dry box with nitrosonium tetrafluoroborate, 1.21 g (10.34 mmole), then transferred to a vacuum line. Acetonitrile was added, (2×50 mL) in order to dissolve the nitrosonium tetrafluoroborate which was transferred (2×50 mL) to the vessel containing the palladium metal slurry. The mixture was stirred at least four hours at room temperature resulting in the formation of a yellow solution of the palladium complex in acetonitrile with trace amounts of suspended metal. The yellow solution was filtered to remove any excess metal residue from the palladium complex prior to use. This complex will be referred to as the cation, I, in the following preparations.

Comparative Example

Preparation of [bis(acetonitrile)palladium(II) 1,3-bis (diphenylphosphino)propane] [tetrafluoroborate], (II.)

The cation, I, was prepared as described above on a 4.70 mmole scale. To a 500 mL vessel in a dry box was added 1,3-bis(diphenylphosphino)propane, 2.13 g (5.12 mmole). The vessel was transferred to a vacuum line and acetonitrile was added, 100 mL. The solution was stirred magnetically during the course of the reaction. I was filtered directly into the vessel containing the phosphine resulting in precipitation of a blood red product. The color faded slowly upon stirring at room temperature resulting in a soluble product which became almost colorless after stirring overnight. All volatiles were removed under vacuum leaving an off-white solid which was washed with hexane (2×100 mL). Hexane was filtered from the solid which was dried completely under vacuum at room temperature for several hours.

Preparation of [bis(acetonitrile)palladium(II) bis{tris(o-methoxyphenyl)phosphine] [tetrafluoroborate], (III.)

The cation, I, was prepared as described on a 4.70 mmole scale. To a 500 mL vessel in a dry box was added tris(o- methoxyphenyl)phosphine, 3.64 g (10.34 mmole), then transferred to a vacuum line. Acetonitrile, 75 mL, was added which partially dissolved the phosphine. The mixture was stirred magnetically at room temperature during the course of the reaction. I was filtered directly into the vessel containing the phosphine causing the solution to darken. The color lightened to a pale yellow after stirring overnight at room temperature. All volatiles were removed under vacuum leaving a solid which was washed with hexane (2×100 mL). The residue was vacuum dried leaving an off-white solid.

Preparation of [bis(acetonitrile)palladium(II) {1,1,1-tris(dimethylphosphinomethyl)ethane}] [tetrafluoroborate], (IV.)

The cation, I, was prepared as described on a 4.70 mmole scale. To a 500 mL vessel in a dry box was weighed 1,1,1-tris(dimethyl phosphinomethyl)ethane, 2.61 g (~2.6 mL or 10.34 mmole), then transferred to a vacuum line. Acetonitrile, 50 mL, was added to the ligand and the mixture was stirred magnetically during the reaction. I was filtered into the vessel containing the phosphine resulting in formation of a red solution. The solution was stirred overnight at room temperature. All volatiles were removed under vacuum leaving a residue which was washed with hexane (2×100 mL). The resulting orange solid was vacuum dried prior to use.

Preparation of [bis(acetonitrile)palladium(II) {1,1,1-tris(diphenylphosphinomethyl)ethane}] [tetrafluoroborate], (V.)

The cation, I, was prepared as described on a 4.70 mmole scale. To a 500 mL vessel in a dry box was added 3.23 g, 5.17 mmole, of 1,1,1-tris(diphenylphosphinomethyl)ethane. The vessel was transferred to a vacuum line and acetonitrile, 100 mL, was added which dissolved the ligand. The mixture was stirred magnetically during the course of the reaction. I was filtered into the vessel containing the phosphine resulting in formation of an orange solution. The mixture was stirred overnight at room temperature. All volatiles were removed under vacuum leaving a powdery residue. The residue was washed with hexane (1×200 mL) then vacuum dry several hours leaving a yellow-orange solid.

Preparation of [bis(acetonitrile)palladium(II) (N,N,N',N'-tetramethyl-1,3-propanediamine)] [tetrafluoroborate], (VI.)

The cation, I, was prepared as described on a 1.88 mmole scale in acetonitrile. A 500 mL vessel was charged with N,N,N',N'-tetramethyl-1,3-propanediamine, 0.48 g (4.14 mmole), and acetonitrile, 75 mL. The contents of the vessel were stirred magnetically during the course of the reaction. I was filtered directly into the vessel containing the bidentate amine. The mixture was stirred overnight at room temperature. All volatiles were removed under vacuum. The remaining red-orange solid was washed with hexane (2×100 mL). The solid was vacuum dried for several hours.

Preparation of [Bis(acetonitrile)palladium(II)-1,3-bis (diphenylphosphino)propane][perchlorate], (VII).

A 100 mL vessel was charged with palladium dichloride, 0.25 g (1.41 mmole) in a dry box then transferred to a vacuum line. A 250 mL vessel was charged with silver perchlorate, 0.64 g (2.82 mmole), in a dry box and transferred to a vacuum line. To the vessel containing PdCl$_2$ was added acetonitrile, 50 mL and the slurry was stirred magnetically. Acetonitrile, 50 mL, was added to the 250 mL vessel containing silver perchlorate. The contents of the vessel were stirred magnetically throughout the procedure. The palladium dichloride slurry was added via canula to the silver perchlorate solution resulting in a gradual formation of a yellow solution over white salts. The mixture was stirred approximately 15 hours at room temperature. A 250 mL vessel was charged with 1,3-bis(diphenylphosphino)propane (DPPP), 0.64 g (1.41 mmole), in a dry box then transferred to a vacuum line. Acetonitrile, 30 mL, was added to the vessel containing DPPP which was stirred for the duration of the following reaction. Stirring was halted of the vessel containing the reaction product of palladium dichloride with silver perchlorate and the salts were allowed to settle from the solution. The solvent phase containing the soluble dication [Pd(CH$_3$CN)$_4$]$^{+2}$[ClO$_4$]$^-_2$ was filtered from the mixture directly into the solution of DPPP in acetonitrile. Additional precipitate formed which became dark blue which is believed to be primarily oxidation products of DPPP with excess AgClO$_4$ and precipitated AgCl. The mixture was stirred 12 hours then allowed to settle in order to separate the precipitate from the solution phase. The yellow solution was filtered from the precipitate and solvent was removed under vacuum. A light yellow-green solid was obtained which appeared crystalline. The solid was washed with hexane (2×30 mL) then vacuum dried (room temperature at 3×10$^{-3}$ Torr).

Preparation of [Bis(dimethylformamide)palladium(II) 1,3-bis (diphenylphosphino)propane][perchlorate], (VIII).

Palladium dichloride, 0.5 g (2.82 mmole), was weighed into a 250 mL Vessel vessel equipped with a magnetic stir bar in a dry box then transferred to a vacuum line. Dimethylformamide, 30 mL, was added to form a slurry of palladium dichloride. Silver perchlorate, 1.29 g (6.20 mmole), was weighed in a dry box into a 100 mL Vessel vessel equipped with a magnetic stir bar then transferred to a vacuum line. Dimethylformamide, 50 mL, was added to the silver perchlorate which dissolved readily with stirring. The silver perchlorate solution was transferred via canula to the stirred slurry containing palladium dichloride resulting in immediate formation of a dark yellow solution over a white-gray precipitate. The mixture was stirred at room temperature approximately 15 hours. Stirring was terminated and the solution was allowed to separate from the salts. A 250 mL vessel equipped with a magnetic stir bar was charged, in a dry box, with 1,3-bis(diphenylphosphino)propane (DPPP), 1.28 g (2.82 mmole), then transferred to a vacuum line. Dimethylformamaide, 30 mL, was added to the DPPP while stirring partially dissolving the sample. The reaction product of silver perchlorate with palladium dichloride was filtered from the precipitate in to the vessel containing DPPP. The remaining DPPP rapidly dissolved and a bright yellow solution immediately formed. The solution was stirred approximately 2 hours then placed under vacuum at 40° C. to remove excess solvent. A gummy yellow brown product was obtained which was washed with hexane (2×50 mL) then vacuum dried. The final product was a fine beige powder.

Preparation of [Bis(benzonitrile)palladium(II)1,3-bis (diphenylphosphino)propane][tetrafluoroborate], (IX).

A 100 mL vessel was charged in a dry box with palladium powder, 0.25 g (2.35 mmole), then transferred to a vacuum line. Benzonitrile, 20 mL was added to the vessel to form a slurry of finely divided metal which was stirred magnetically. A 100 mL vessel was charged in a dry box with nitrosonium tetrafluoroborate, 0.60 g (5.17 mmole), then transferred to a vacuum line. Benzonitrile, 20 mL was added to form a solution which was stirred magnetically. The nitrosonium tetrafluoroborate was added via canula to the Pd slurry and the mixture was allowed to react for three days. The mixture was then heated to 50° C. for four hours to complete the reaction. An orange-yellow suspension was obtained. A 250 mL vessel was charged with 1,3-bis(diphenylphosphino)propane (DPPP), 1.07 g (2.58 mmole) in a dry box then transferred to a vacuum line. Benzonitrile, 20 mL, was added to the vessel containing DPPP which was stirred magnetically. The vessel containing the reaction product of palladium with NOBF$_4$ was added via canula to the vessel containing DPPP. A yellow-orange solution formed over precipitate which was stirred 2 hours. The mixture was filtered from the solid and hexane, 50 mL, was added to the filtered solution resulting in precipitation of a beige powder. The powder was washed with hexane (3×20 mL) then dried under vacuum several hours at room temperature prior to use.

Preparation of [Bis(propionitrile)palladium(II)1,3
-bis(diphenylphosphino)propane][tetrafluoroborate],
(X).

A 100 mL vessel was charged in a dry box with palladium powder, 0.25 g (2.35 mmole), then transferred to a vacuum line. Propionitrile, 25 mL was added to the vessel to form a slurry of finely divided metal which was stirred magnetically. A 100 mL vessel was charged in a dry box with nitrosonium tetrafluoroborate, 0.60 g (5.17 mmole), then transferred to a vacuum line. Propionitrile, 25 mL was added to form a solution which was stirred magnetically. The nitrosonium tetrafluoroborate was added via canula to the Pd slurry resulting in rapid formation of an olive colored solution. The mixture was allowed to react for four hours with some precipitate formation noted. A 250 mL vessel was charged with 1,3-bis(diphenylphosphino)propane (DPPP), 1.07 g (2.58 mmole) in a dry box then transferred to a vacuum line. Propionitrile, 25 mL, was added to the vessel containing DPPP which was stirred magnetically. The vessel containing the reaction product of palladium with NOBF$_4$ was added via canula to the vessel containing DPPP. The mixture was stirred 4 hours and additional precipitate formation was noted. The solution was filtered into a 100 mL vessel and precipitated with hexane, 35 mL, after volume reduction under vacuum. An off-white to gold colored powder was obtained which was washed with hexane (3×25 mL) then dried several hours under vacuum prior to use.

Preparation of [Bis(acetonitrile)palladium(II)1.3
-bis(diphenylphosphino)propane]
[hexafluorophosphate], (XI).

A 250 mL vessel was charged in a dry box with palladium dichloride, 0.25 g (1.42 mmole), then transferred to a vacuum line. Acetonitrile, 30 mL, was added to the vessel to form a slurry which was stirred magnetically. A 100 mL vessel was charged in a dry box with sodium hexafluorophosphate, 0.52 g (3.10 mmole), then transferred to a vacuum line. Acetonitrile, 30 mL, was added to form a solution/slurry which was stirred magnetically. Sodium hexafluorophosphate was added to the slurry of PdCl$_2$ then the vessel containing NaPF$_6$ was again rinsed with acetonitrile, 30 mL, which was transferred to the vessel containing PdCl$_2$. The mixture gradually formed a yellow solution which was stirred 15 hours at room temperature. A graywhite precipitate formed with all palladium dichloride being consumed in the reaction. A 250 mL vessel was charged with 1,3-bis(diphenylphosphino)propane (DPPP) in a dry box then transferred to a vacuum line. Acetonitrile, 30 mL, was added and the solution containing the reaction product of palladium dichloride with sodium hexaphophate was filtered in the vessel containing DPPP. The mixture was stirred approximately 2 hours with formation of additional precipitate. All solvent and volatiles were removed under vacuum at room temperature leaving an off-white solid which was washed with hexane (2×50 mL). The powder was dried under vacuum several hours prior to use.

Preparation of
[Dimethoxyethanepalladium(II)1,3-bis
(diphenylphosphino)propane]
[tetrafluoroborate], (XIX).

A 250 mL vessel was charged in a dry box with palladium powder, 0.25 g (2.35 mmole), then transferred to a vacuum line. Dimethoxyethane, 25 mL, was added to the vessel to form a slurry of finely divided metal which was stirred magnetically. A 100 mL vessel was charged in a dry box with nitrosonium tetrafluoroborate, 0.60 g (5.17 mmole), then transferred to a vacuum line. 1,2-Dimethoxyethane, 50 mL, was added to form a solution which was stirred magnetically. The nitrosonium tetrafluoroborate was added via canula to the Pd slurry resulting in rapid formation of a yellow-green solution. The mixture was allowed to react for 15 hours with a slight amount of precipitate formation noted. A 250 mL vessel was charged with 1,3-bis(diphenylphosphino)propane (DPPP), 1.07 g (2.58 mmole) in a dry box then transferred to a vacuum line. Dimethoxyethane, 50 mL, was added to the vessel containing DPPP which was stirred magnetically. The vessel containing the reaction product of palladium with NOBF$_4$ was added via canula to the vessel containing DPPP. The mixture was stirred 4 hours with formation of a bright yellow solution over white precipitate. The solution was filtered from the solids and volatiles were removed under vacuum. The sticky solid was washed with hexane (2×50 mL) followed by dissolution in 1,2-dimethoxyethane, 50 mL, then addition of hexane, 100 mL, resulting in formation of a yellow precipitate which was washed with hexane (3×50 mL) followed by vacuum drying prior to use.

Preparation of
[Bis(acetonitrile)palladium(II)-1,3-bis
(diphenylphosphino)propane]
[trifluoromethanesulfonate], (XIII).

Palladium dichloride, 0.25 g (1.41 mole), and silver trifluoromethanesulfonate, 0.80 g (3.10 mole), were weighed in a dry box and transferred to a 250 mL vessel equipped with a magnetic stir bar. The flask was transferred to a vacuum line and acetonitrile, 75 mL, was added to the mixture which was stirred magnetically for the duration of the procedure. The solution phase gradually became yellow with formation of an off-white precipitate. 1,3-Bis(diphenylphosphino)propane (DPPP), 0.64 g (1.55 mole), was weighed in a dry box into a 250 mL vessel then transferred to a vacuum line. The light yellow solution phase was filtered from the precipitate into the flask containing DPPP and the mixture was stirred overnight at room temperature. The color essentially disappeared with only a trace of yellow color evident in the mixture, additional precipitate formed in the reaction product. The solution phase was separated from the precipitate by filtration into a 250 mL flask then all volatiles were removed under vacuum at room temperature. An off-white to light gray solid remained which was washed with hexane (2×25 mL). The solid was further dried under vacuum prior to use.

POLYMERIZATION

A 450 mL stainless steel (316-SS) reactor purchased from Parr Instrument Company was used for the copolymerization of carbon monoxide with olefins. The reactor was fitted with an internal cooling loop for heat removal and a double stacked arrangement of four blade stirrers. Temperature was controlled, unless otherwise noted, by a PID (proportional-integral-derivative) controller which predicts cooling and heating as a function of the rate and trend of temperature changes during the polymerization and the temperature setpoint. Moisture and oxygen were removed, unless otherwise noted, from the reactor surfaces by heating the cylinder and stirrer assemblies at least 12 hours at 120° C. in a convection oven, followed by assembly of these components under a high purity nitrogen purge. As noted in the examples, further drying was effected by heating the vessel under nitrogen to 200° C. then releasing the pressure followed by evacuation of the vessel with a vacuum pump. The heating and vacuum cycles were repeated a total of three times. This is referred to as charging under inert conditions in the example.

For some polymerization runs, except as noted, all catalyst components and solvents were handled and transferred under dry nitrogen. Catalyst was transferred and weighed in a dry box into a four ounce bottle fitted with a rubber septum. Solvent, generally 50–100 mL, was transferred to the catalyst bottle in order to dissolve the solid under dry nitrogen using standard airless transfer. Catalyst was transferred to the reactor, as well as promoter and solvent, through a 100 mL capacity pressure addition vessel. The vessel was maintained under an inert atmosphere during the transfer and the liquid contents were forced into the reactor under high (750–1000 psig) nitrogen pressure. Each component was added to the reactor in the following order unless otherwise noted; 1) promoter (methanol), 2) solvent and 3) catalyst in solvent. The reactor was vented to atmospheric pressure after each addition. Propylene and/or ethylene was next added to the reactor to give the desired partial pressure followed by carbon monoxide at which time the reaction commenced. All reaction times are based on the time at which the last component, carbon monoxide, was added to the reactor. For runs made without consideration of transferring the reaction components under nitrogen, the reactor was charged at room temperature by adding in air to the reactor cylinder catalyst dissolved in the run solvent, methanol and solvent. The cylinder was then attached to the reactor head and briefly purged with nitrogen or gaseous olefin prior to charging. Propylene and/or ethylene was next added to the reactor to give the desired partial pressure of each component. The reactor was heated to or within a few degrees of the desired setpoint and carbon monoxide was added to give the desired total pressure. All reaction time are based on the time at which carbon monoxide was added to the reactor. The mixture was stirred at 1000 rpm for the duration of the run. At the end of the polymerization, pressure was released from the reactor to terminate the reaction and product was removed by disassembling the cylinder from the reactor head and pouring-off the product. Solvent was devolatilized from the polymer overnight in a fume hood then further dried in a vacuum oven for at least 48 hours at 60°–90° C. No stabilizers or antioxidants were added to the products.

Reaction Solvents

Tetrahydrofuran, diethyl ether and 1,2-dimethoxyethane were purchased from Aldrich in Kilo-Lab cylinders then dried by refluxing over Na/K alloy in the presence of benzophenone to produce the Na/K benzophenone ketal radical anion. Solvent was distilled from the above mixture. Toluene was obtained from Fisher and dried over 4A molecular sieves followed by reflux and distillation from molten Na. Chloroform, methylene chloride, 1,2-dichloroethane and acetonitrile were purchased as anhydrous form Aldrich in Sure Seal Bottles and used without further purification. Acetone was obtained as reagent grade in 55 gallon drums from Delta Distributors and used without further purification. Absolute methanol was obtained from Fisher and purged with nitrogen followed by the addition of Mg turnings to produce magnesium methoxide. Anhydrous methanol was distilled from the mixture under dry nitrogen followed by the addition of more Mg turnings then distillation of the product under dry nitrogen. All anhydrous solvents were stored under dry nitrogen.

The invention is further illustrated by the following Comparative Examples (not of the invention) and the following Illustrative Examples which should not be regarded as limiting. The polymer products of the Comparative and Illustrative Examples were examined by $^{13}C$ NMR and/or infrared spectroscopy. All copolymer products were found to be linear alternating copolymers of carbon monoxide and ethylene and all terpolymer products were found to be linear alternating terpolymers of carbon monoxide and ethylene or propylene.

ILLUSTRATIVE EXAMPLE 1

The reactor was charged under inert conditions as previously described with 0.2 mmole of III, 1,2-dichloroethane, 150 mL, methanol, 10 mL, octene, 50 mL and carbon monoxide, 821 psig at 20° C. The mixture was stirred 25 hours with no heating. Approximately 1 g of polymer was recovered from the reactor. The polymerization rate was 2 g of polymer/g-Pd/hr.

ILLUSTRATIVE EXAMPLE 2

The reactor was charged under inert conditions as previously described with 0.2 mmole of IV, 1,2-dichloroethane, 150 mL, methanol, 10 mL, octene, 50 mL and carbon monoxide, 820 psig at 23° C. The mixture was stirred 24 hours with no heating. A trace amount of polymer was recovered from the reactor.

ILLUSTRATIVE EXAMPLE 3

The reactor was charged under inert conditions as previously described with 0.2 mmole of V, 1,2-dichloroethane, 135 mL, methanol, 10 mL, propylene, 80 psig at 19° C. and enough carbon monoxide to give a total reactor pressure of 906 psig at 17° C. The mixture was stirred 24 hours and 50 minutes with no heating. A total of 13.68 g of polymer was recovered from the reactor. The polymerization rate was 26 g of polymer/g-Pd/hr.

ILLUSTRATIVE EXAMPLE 4

The reactor was charged under inert conditions as previously described with 0.2 mmole of VI, 1,2-dichloroethane, 150 mL, methanol, 10 mL, ethylene, 275 psig at 24° C. and enough carbon monoxide to give a total reactor pressure of 1012 psig at 24° C. The mixture was stirred 29 hours and 26 minutes with no heating. A total of 0.30 g of polymer was recovered from the reactor. The polymerization rate was 0.5 g of polymer/g-Pd/hr.

ILLUSTRATIVE EXAMPLE 5

The reactor was charged under atmospheric conditions with no consideration against air or moisture exposure as previously described with 0.12 mmole of VII, 1,2-dichloroethane, 150 mL, methanol, 5 mL, ethylene 214 psig at 18° C. and enough carbon monoxide was added to give a total reactor pressure of 914 psig at 32° C. Initially, the reactor setpoint was 45° C. The final setpoint was 100° C. with a maximum temperature of 102° C. observed during the run. The mixture was allowed to stir 51 minutes prior to termination. Two additional carbon monoxide charges were made during the course of the reaction. A total of 25.87 g of polymer was collected. The polymerization rate was 2,384 g of polymer/g-Pd/hr.

ILLUSTRATIVE EXAMPLE 6

The reactor was charged under atmospheric conditions with no consideration against air or moisture exposure as previously described with 0.12 mmole of VII, acetone, 150 mL, methanol, 10 mL, ethylene, 229 psig at 24° C. and enough carbon monoxide was added to give a total reactor pressure of 920 psig at 25° C. Initially, the reactor setpoint was 45° C. The final setpoint was 80° C. with a maximum temperature of 83° C. observed during the run. The mixture was allowed to stir for 1 hour prior to termination. Two additional carbon monoxide charges were made during the course of the reaction. A total of 35.98 g of polymer was collected. The polymerization rate was 2,818 g of polymer/g-Pd/hr.

ILLUSTRATIVE EXAMPLE 7

The reactor was charged under atmospheric conditions with no consideration against air or moisture exposure as previously described with 0.12 mmole of VII, methanol, 150 mL ethylene, 119 psig at 20° C. and enough carbon monoxide was added to give a total reactor pressure of 900 psig at 25° C. Initially, the reactor setpoint was 45° C. The final setpoint was 80° C., however, the reaction was terminated prior to reaching setpoint and the maximum temperature observed was 77° C. The mixture was allowed to stir 40 minutes prior to termination. One additional carbon monoxide charge was made during the course of the reaction. A total of 13.17 g of polymer was collected. The polymerization rate was 1,547 g of polymer/g-Pd/hr.

ILLUSTRATIVE EXAMPLE 8

The reactor was charged under atmospheric conditions with no consideration against air or moisture exposure as previously described with 0.012 mmole of VIII, acetone, 150 mL methanol, 1 mL, ethylene, 211 psig at 12° C. and enough carbon monoxide was added to give a total reactor pressure of 985 psig at 47° C. The reactor setpoint was 80° C., carbon monoxide was added during heating when the reactor reached 45° C. A maximum reactor temperature of 82° C. was observed during the polymerization run. The mixture was allowed to stir 7 hours and 20 minutes prior to termination. The catalyst was still active as indicated by the continued drop in total pressure. Two additional carbon monoxide charges were made during the course of the reaction. A total of 28.84 g of polymer was collected. The polymerization rate was 3,080 g of polymer/g-Pd/hr.

ILLUSTRATIVE EXAMPLE 9

The reactor was charged under atmospheric conditions with no consideration against air or moisture exposure as previously described with 0.17 mmole of IX, 1,2-dichloroethane, 100 mL, methanol, 10 mL, ethylene, 215 psig at 24° C. and enough carbon monoxide was added to give a total reactor pressure of 1002 psig at 52° C. The reactor setpoint was 65° C., carbon monoxide was added during heating when the reactor reached 45° C. A maximum temperature of 70° C. was observed during the run. The mixture was allowed to stir 1 hour and 35 minutes prior to termination. The catalyst was still active at the end of the run. Two additional carbon monoxide charges were made during the course of the reaction. A total of 28.35 g of polymer was collected. The polymerization rated was 1,008 g of polymer/g-Pd/hr.

ILLUSTRATIVE EXAMPLE 10

The reactor was charged under atmospheric conditions with no consideration against air or moisture exposure as previously described with 0.19 mmole of X, 1,2-dichloroethane, 150 mL, methanol, 10 mL, ethylene, 216 psig at 21° C. and enough carbon monoxide was added to give a total reactor pressure of 1001 psig at 49° C. The reactor setpoint was 65° C., carbon monoxide was added during heating when the reactor reached 45° C. A maximum temperature of 66° C. was observed during the run. The mixture was allowed to stir 1 hour and 11 minutes prior to termination. The catalyst was still active at the end of the run. One additional carbon monoxide charge was made during the course of the reaction. A total of 18.14 g of polymer was collected. The polymerization rated was 771 g of polymer/g-Pd/hr.

ILLUSTRATIVE EXAMPLE 11

The reactor was charged under atmospheric conditions with no consideration against air or moisture exposure as previously described with 0.17 mmole of XI, 1,2-dichloroethane, 150 mL, methanol, 10 mL, ethylene, 224 psig at 28° C. and enough carbon monoxide was added to give a total reactor pressure of 1023 psig at 49° C. The reactor setpoint was 65° C., carbon monoxide was added during heating when the reactor reached 45° C. The reactor temperature was increased to 75° C. after 24 minutes then to 90° C. after a total run time of 38 minutes. The mixture was allowed to stir 47 minutes prior to termination. A trace of polymer was obtained.

ILLUSTRATIVE EXAMPLE 12

The reactor was charged under atmospheric conditions with no consideration against air or moisture exposure as previously described with 0.17 mmole of XI, acetonitrile, 150 mL, methanol, 10 mL, ethylene, 222 psig at 26° C. and enough carbon monoxide was added to give a total reactor pressure of 1001 psig at 50° C. The reactor setpoint was 65° C., carbon monoxide was added during heating when the reactor reached 45° C. The mixture was allowed to stir 43 minutes prior to termination. No polymer was obtained, however, some oligomeric product was evident from a sticky coating on the reactor surfaces.

ILLUSTRATIVE EXAMPLE 13

The reactor was charged under atmospheric conditions with no consideration against air or moisture exposure as previously described with 0.19 mmole of XII, 1,2-dichloroethane, 150 mL, methanol, 10 mL, ethylene, 226 psig at 31° C. and enough carbon monoxide was added to give a total reactor pressure of 1004 psig at 49° C. The reactor setpoint was 65° C., carbon monoxide was added during heating when the reactor reached 45° C. The mixture was allowed to stir 2 hours and 6 minutes prior to termination. A trace of polymer was obtained.

ILLUSTRATIVE EXAMPLE 14

The reactor was charged under atmospheric conditions with no consideration against air or moisture exposure as previously descrived with 0.12 mmole of VIII, acetone, 150 mL, methanol, 10 mL, propylene, 76 psig at 25° C., enough ethylene to give a combined propylene+ethylene pressure of 224 psig at 26° C. and enough carbon monoxide to give a combined propylene+ethylene+carbon monoxide pressure of 1026 psig at 72° C. The reactor setpoint was 100° C. with a maximum temperature of 101° C. observed during the run. The mixture was allowed to stir 2 hours and 18 minutes prior to termination. Two additional carbon monxide charges were made to the reactor during the course of the reaction. A total of 31.48 g of polymer was collected. The polymerization rate was 1,072 g of polymer/g-Pd/hr. Analysis showed 9.31 mole percent of the polymer consisted of incorporated propylene.

ILLUSTRATIVE EXAMPLE 15

The reactor was charged under atmospheric conditions with no consideration against air or moisture exposure as previously described with 0.11 mmole of XIII, acetone, 150 mL, methanol, 10 mL, ethylene 210 psig at 18° C. and enough carbon monoxide to give a total reactor pressure of 1036 psig at 19° C. The reactor setpoint was initially 50° C. then raised to 65° C. after 12 minutes then raised to 80° C. after 23 minutes. Two additional charges of carbon monoxide were to the reactor during the course of the reaction. The mixture was allowed to stir 1 hour and 7 minutes prior to termination. A total of 36.35 g of polymer was collected. The polymerization rate was 2,898 g of polymer/g-Pd/hr.

In the following Comparative Examples [bis(acetonitrile-)palladium(II)1,3-bis(diphenylphosphino)propane] [tetrafluoroborate] as taught by Sen is used to demonstrate that polar solvents lower the catalytic activity of this catalyst. Additonally, at process temperatures above 65° C., catalyst activity and polymerization rate are decreased significantly. In contrast, these parameters do not substantially lower the catalytic activity of the catalysts corresponding to the present invention.

COMPARATIVE EXAMPLE 1

The reactor was charged under inert conditions as previously described with 0.2 mmole of II, 1,2,-dichloroethane, 150 mL, methanol, 10 mL, octene, 50 mL and carbon monoxide 810 psig at 26° C. The mixture was stirred 22 hours and 15 minutes at with no heating. A total of 11.40 g of polymer was recovered from the reactor. The polymerization rate was 24 g of polymer/g-Pd/hr.

COMPARATIVE EXAMPLE 2

The reactor was charged under inert conditions as previously described with 0.2 mmole of II, 1,2-dichloroethane, 150 mL, methanol, 10 mL, propylene, 80 psig at 17° C. and enough carbon monoxide to give a total reactor pressure of 1001 psig at 17° C. An additional carbon monoxide charge was made during the course of the polymerization due to consumption by polymerization. The mixture was stirred 27 hours and 30 minutes with no heating. A total of 51.05 g of polymer was recovered from the reactor. The polymerization rate was 87 g of polymer/g-Pd/hr.

COMPARATIVE EXAMPLE 3

The reactor was charged under inert conditions as previously described with 0.2 mmole of II, acetonitrile, 150 mL, methanol, 10 mL, propylene, 90 psig at 15° C. and enough carbon monoxide to give a total reactor pressure of 907 psig at 15° C. The reaction was allowed to stir for 33 hours and 55 minutes prior to termination with no heating. A total of 0.80 g of polymer was recovered from the reactor. The polymerization rate was 1 g of polymer/g-Pd/hr.

COMPARATIVE EXAMPLE 4

The reactor was charged under inert conditions as previously described with 0.2 mmole of II, chloroform, 150 mL, methanol, 10 mL, propylene, 76 psig at 19° C. and enough carbon monoxide to give a total reactor pressure of 929 psig at 18° C. The reaction was allowed to stir for 24 hours and 5 minutes prior to termination with no heating. A total of 25.412 g of polymer was recovered from the reactor. The polymerization rate was 24 g of polymer/g-Pd/hr.

COMPARATIVE EXAMPLE 5

The reactor was charged under inert conditions as previously described with 0.2 mmole of II, methylene chloride, 150 mL, methanol, 10 mL, propylene, 76 psig at 20° C. and enough carbon monoxide to give a total reactor pressure of 931 psig at 17° C. The reaction was allowed to stir for 24 hours prior to termination with no heating. A total of 27.172 g of polymer was recovered from the reactor. The polymerization rate was 53 g of copolymer/g-Pd/hr.

COMPARATIVE EXAMPLE 6

The reactor was charged under inert conditions as previously described with 0.2 mmole of II, tetrahydrofuran, 150 mL, methanol, 10 mL, propylene, 78 psig at 18° C. and enough carbon monoxide to give a total reactor pressure of 909 psig at 18° C. The reaction was allowed to stir 19 hours and 30 minutes prior to termination with no heating. A total of 10.41 g of polymer was recovered from the reactor. The polymerization rate was 25 g of polymer/g-Pd/hr.

COMPARATIVE EXAMPLE 7

The reactor was charged under inert conditions as previously described with 0.2 mmole of II, 1,2-dimethoxyethane, 150 mL, methanol, 10 mL, propylene, 86 psig at 22° C. and enough carbon monoxide to give a total reactor pressure of 945 psig at 18° C. The reaction was allowed to stir 24 hours and 15 minutes prior to termination with no heating. A total of 6.08 g of polymer was recovered from the reactor. The polymerization rate was 12 g of polymer/g-Pd/hr.

COMPARATIVE EXAMPLE 8

The reactor was charged under inert conditions as previously described with 0.2 mmole of II, methanol, 150 mL, propylene, 94 psig at 18° C. and enough carbon monoxide to give a total reactor pressure of 905 psig at 17° C. The reaction was allowed to stir 24 hours and 5 minutes prior to termination with no heating. A total of 3.25 g of polymer was recovered from the reactor. The polymerization rate was 6 g of polymer/g-Pd/hr.

COMPARATIVE EXAMPLE 9

The reactor was charged under inert conditions as previously described with 0.2 mmole of II, 1,2-dichloroethane, 150 mL, propylene, 80 psig at 18° C. and enough carbon monoxide to give a total reactor pressure of 1002 psig at 16° C. The reaction was allowed to stir 24 hours and 25 minutes prior to termination with no heating. A total of 3.49 g of polymer was recovered from the reactor. The polymerization rate was 24 g of polymer/g-Pd/hr.

COMPARATIVE EXAMPLE 10

The reactor was charged under inert conditions as previously described with 0.2 mmole of II, 1,2-dichloroethane, 150 mL, methanol, 10 mL, propylene, 77 psig at 19° C. and enough carbon monoxide to give a total reactor pressure of 902 psig at 125° C. A total of 15 minutes was required to reach the reactor setpoint of 125° C. after charging carbon monoxide to the reactor. The reaction was allowed to stir 2 hours and 30 minutes prior to termination, the catalyst showed no significant activity at the end of the run. A total of 9.05 g of polymer was recovered from the reactor. The polymerization rate was 170 g of polymer/g-Pd/hr.

COMPARATIVE EXAMPLE 11

The reactor was charged under inert conditions as previously described with 0.2 mmole of II, 1,2-dichloroethane, 150 mL, methanol, 10 mL, ethylene, 271 psig at 39° C. and enough carbon monoxide to give a reactor pressure of 1150 psig at 54° C. The reactor was heated to 45° C. prior to carbon monoxide addition. The setpoint for the reaction was 65° C. An exotherm of 8° C. above the setpoint was observed after 3 minutes. The reaction was allowed to stir 2 hours and 51 minutes prior to termination. A total of 30.71 g of polymer was recovered from the reactor. The polymerization rate was 506 g of polymer/g-Pd/hr.

What is claimed is:

1. A homogeneous catalyst composition consisting essentially of a cationic transition metal complex of the formula $$(Pd(II)S_{4-ax}L_x)^{+2}(A)^{-n}{}_y$$

wherein:

Pd(II) is palladium having a valence of +2;

S is tetrahydrofuran, 1,2-dimethoxyethane, pyridine, acetonitrile, propionitrile, benzonitrile, dimethylformamide, hexamethylphosphoramide, dimethylsulfoxide, 1-piperidinecarbonitrile or a mixture thereof;

L is a monodendate, bidendate or tridendate ligand or ligands having one or more bonding sites;

x is an integer from 1 to 3 and is equal to the total number of ligands;

A is a weakly or non-coordinating anion capable of stabilizing the complex in its cationic form, wherein A is selected from tetrafluoroborate, perchlorate, tetraphenylborate, hexafluorophosphate, trifluoromethanesulfonate, or a mixture thereof;

a represents the number of bonding sites of the ligand L; and n is 1 or 2 and y is 2 or 1;

provided that (i) when n is 1, y is 2 and when n is 2, y is 1; and (ii) when the anion A is tetrafluoroborate, the organometallic complex is not (tris(acetonitrile)palladium (II)triphenylphosphine), (bis(acetonitrile)palladium(II) bis-(triphenyl-phosphine)), ((acetonitrile)palladium(II) tris(triphenylphosphine)) (bis(acetonitrile)palladium(II) 1,3-bis(diphenylphosphino)propane) or bis(pyridine) palladium(II)bis(diphenylphosphino)ethane.

2. The composition of claim 1 wherein L contains nitrogen, phosphorous, arsenic or antimony.

3. The composition of claim 2 wherein L is 1,3-bis(diphenylphosphino)propane and A is perchlorate or tetrafluoroborate, with the proviso that when A is perchlorate, S is acetonitrile or dimethylformamide and when A is tetrafluoroborate, S is benzonitrile or propionitrile.

4. The composition of claim 3 wherein the organometallic complex is (bis(acetonitrile)palladium(II) 1,3-bis(diphenylphosphino)propane) and A is (perchlorate).

5. A homogeneous catalyst composition consisting essentially of a cationic transition metal complex of the formula $$(Pd(II)S_{4-ax}L_x)^{+2}(A)^{-n}{}_y$$

wherein:

Pd(II) is palladium having a valence of +2;

S is acetonitrile, benzonitrile, propionitrile, 1,4-dioxane, dimethylformamide, hexamethylphosphoramide, pyridine, 1-piperidinecarbonitrile, dimethoxyether, aniline, dimethylsulfoxide, 1,2-dimethoxyethane, diethylether, tetrahydrofuran, or a mixture of at least two thereof;

L is a substantially water insoluble monodendate, bidendate or tridendate ligand or ligands having one or more bonding sites;

x is an integer from 1 to 3 and is equal to the total number of ligands;

A is a weakly or non-coordinating anion capable stabilizing the complex in its cationic form, wherein A is selected from tetrafluoroborate, perchlorate, tetraphenylborate, hexafluorophosphate, trifluoromethanesulfonate, or a mixture thereof;

a represents the number of bonding sites of the ligand L; and n is 1 or 2 and y is 2 or 1;

provided that (i) when n is 1, y is 2 and when n is 2, y is 1; and (ii) when the anion A is tetrafluoroborate, the organometallic complex is not (tris(acetonitrile)palladium (II)triphenylphosphine), (bis(acetonitrile)palladium(II) bis-(triphenyl-phosphine)), ((acetonitrile)palladium(II)tris(triphenylphosphine)) (bis(acetonitrile)palladium(II) 1,3-bis(diphenylphosphino)propane) or bis(pyridine)palladium(II)bis-(diphenylphosphino)ethane.

6. The composition of claim 5 wherein L contains nitrogen, phosphorous, arsenic or antimony.

7. The composition of claim 6 wherein S is tetrahydrofuran, 1,2-dimethoxyethane, pyridine, acetonitrile, propionitrile, benzonitrile, dimethylformamide, hexamethylphosphoramide, dimethylsulfoxide, or 1-piperidinecarbonitrile, and A is tetrafluoroborate, perchlorate, tetraphenylborate, hexafluorophosphate, or trifluoromethanesulfonate.

8. The composition of claim 5 wherein the organometallic complex is (bis(acetonitrile)palladium(II) 1,3-bis(diphenylphosphino)propane) and A is (trifluoromethanesulfonate).

9. A homogeneous catalyst composition consisting essentially of a cationic transition metal complex of the formula $$(Pd(II)S_{4-ax}L_x)^{+2}(A)^{-n}{}_y$$

wherein:

Pd(II) is palladium having a valence of +2;

S is tetrahydrofuran, 1,2-dimethoxyethane, pyridine, acetonitrile, propionitrile, benzonitrile, dimethylformamide, hexamethylphosphoramide, dimethylsulfoxide, 1- piperidinecarbonitrile or a mixture thereof;

L is a monodendate, bidendate or tridendate ligand or ligands having one or more bonding sites;

x is an integer from 1 to 3 and is equal to the total number of ligands;

A is a weakly or non-coordinating anion capable of stabilizing the complex in its cationic form, wherein A is selected from tetrafluoroborate, perchlorate, tetraphenylborate, hexafluorophosphate, triflouromethanesulfonate, or a mixture thereof;

a represents the number of bonding sites of the ligand L; and n is 1 or 2 and y is 2 or 1;

provided that (i) when n is 1, y is 2 and when n is 2, y is 1; and (ii) when the anion A is tetrafluoroborate, the organometallic complex is not (tris(acetonitrile)palladium (II)triphenylphosphine), (bis(acetonitrile)palladium(II) bis(triphenyl-phosphine)), ((acetonitrile)palladium(II)tris(triphenylphosphine)) (bis(acetonitrile)palladium(II) 1,3-bis(diphenylphosphino)propane) or bis(pyridine)palladium(II)bis(diphenylphosphino)ethane; and (iii) when the anion A is perchlorate, the ligand L is not 1,3-bi(di-n-butylphosphine) propane.

* * * * *